United States Patent [19]

Frey

[11] 4,221,324

[45] Sep. 9, 1980

[54] CENTRIFUGE WITH VARIABLE ANGLE OF ATTACK

[76] Inventor: Raymond Frey, Zürich, Switzerland

[21] Appl. No.: 964,082

[22] Filed: Nov. 27, 1978

[30] Foreign Application Priority Data

Dec. 5, 1977 [CH] Switzerland ............... 14831/77

[51] Int. Cl.² ............................................ B04B 7/02
[52] U.S. Cl. ................................................... 233/26
[58] Field of Search .......................... 233/25, 26, 11; 164/287, 289, 290

[56] References Cited

U.S. PATENT DOCUMENTS

| | | | |
|---|---|---|---|
| 3,722,789 | 3/1973 | Kennedy | 233/26 |
| 3,951,334 | 4/1976 | Fleming et al. | 233/26 |

Primary Examiner—George H. Krizmanich

Attorney, Agent, or Firm—Werner W. Kleeman

[57] ABSTRACT

A centrifuge with variable angle of attack or positioning angle containing pivotable holders for centrifuge tubes or the like which contain a sample. At the centrifuge rotor there are arranged stops for limiting the outward pivoting of the holders. The position of the stops is variable. The stops are preferably assembled together into a ring which is displaceable and fixable in position at the rotor. The stops optionally can also be merely assembled together into groups. The ring can be structured at its lower part so as to have a sawtooth-shape or with steps. By means of a scale there can be indicated the position of the stops. The centrifuge preferably is employed for separating erythrocytes in a blood sample, and generally can be used for separating particles suspended in a liquid.

4 Claims, 7 Drawing Figures

CENTRIFUGE WITH VARIABLE ANGLE OF ATTACK

BACKGROUND OF THE INVENTION

The present invention relates to a new and improved construction of centrifuge for separating particles suspended in a liquid, particularly although not exclusively for the separation of erythrocytes in a blood sample.

For the electronic counting of thrombocytes contained in a blood sample it is advantageous to initially remove as many erythrocytes as possible from the blood sample. The erythrocytes are more numerous and much larger than the thrombocytes so that they can disturb the measurement operation. It is known for the purpose of removing the erythrocytes to centrifuge the blood sample. The erythrocytes settle in a sediment and the remaining liquid is more suitable for counting the thrombocytes than the non-centrifuged sample.

A centrifuge is known to the art wherein the centrifuge tubes are supported at the rotor in such a fashion that their lengthwise axes intersect the rotational axis of the rotor at a constant small angle, for instance amounting to about 3°. The centrifuge tubes are not pivotably arranged at the rotor. With this construction the centrifugal force acts approximately transversely with respect to the tube axis, so that in the case of centrifuge tubes containing whole blood the erythrocytes migrate along a short path (at most amounting to the diameter of the tubes) and therefore tend to correspondingly rapidly collect at the side of the tube wall facing away from the axis of rotation of the rotor. Additionally, the curvature of the tube wall favors a particularly dense collection of the erythrocytes, so that as is known there occurs an aggregation of the erythrocytes which is referred to in the art as "nummulation" or "rouleaux formation." Such formed aggregates or "rouleaux formations" possess a significantly greater sedimentation speed than the individual erythrocytes. What is disadvantageous is that the sediment, during centrifuging, deposits along the total filling height of the centrifuge tube. After stopping of the rotor the sediment migrates to the floor of the centrifuge tube. This firstly requires time and secondly causes a partial remixing or resuspension or the erythrocytes. It has been observed that sediment and residual material (remaining liquid) are not separated by a clearly defined separation surface or interface, and that the residual material, which is poor in erythrocytes, is extremely small percentually with respect to the total sample volume. The removal of a small poor in erythrocytes from this residual material is therefore extremely critical, since the currents or flow which is formed during pipetting also floats-in erythrocytes from the sediment in an uncontrolled manner. The erythrocyte concentration in the pipetted sample therefore is subjected to large fluctuations.

Another construction of centrifuge is known to the art wherein the centrifuge tubes likewise are not pivotably arranged at the rotor. The lengthwise axis of the centrifuge tubes intersects with the rotational axis of the rotor at a constant, larger angle, for instance amounting to about 30°. With this arrangement the sediment already collects at the region of the tube base during centrifuging. What is disadvantageous, however, is that the erythrocytes migrate over a longer path, than in the case of an almost vertical position of the lengthwise axis of the centrifuge tube, before there is favored the rouleaux formation, so that sedimentation lasts for a longer period of time under the action of the centrifugal force. This again is disadvantageous inasmuch as loading of the cells by the action of the centrifugal force causes a morphological change of the cells which is progressive in the static sense. Additionally, also disadvantageous is the fact that during centrifuging the separation surface or interface which forms between the sediment and the remaining or residual material extends approximately vertically, and therefore, at an inclination to the lengthwise axis of the centrifuge tube. If the centrifuge tube, following stoppage of the rotor, remains for a while in situ, then there is formed a horizontal separation surface, which, however, likewise is inclined with respect to the lengthwise axis of the centrifuge tube. If the centrifuge tube is removed from the centrifuge immediately upon standstill of the rotor or later, then it is placed in a stand which normally is provided for a vertical tube axis, and there is again formed a horizontal separation surface, i.e., extending transversely with respect to the tube axis. As should be apparent there occurs at least once a remixing effect, which, while less prounouced than with the first described centrifuge construction, still the previously mentioned drawbacks essentially are also present here.

Additionally, a centrifuge has been disclosed to the art wherein the centrifuge tubes are pivotably mounted and can shift, under the action of the centrifugal force, from a vertical position into an almost horizontal position. With this arrangement the centrifugal force acts, as desired, in the direction of the tube axis and the tube floor or base. What is disadvantageous however is that the erythrocytes migrate over a longer path, which can amount to the total filling height of the centrifuge tube. This counteracts or completely elminates the rapid rouleaux formation if the sample consists of diluted blood, since the rouleaux formation only arises at those locations where the dilution of the erythrocytes does not exceed a ratio of about 1:5. Furthermore, what is additionally disadvantageous is that the displacement flow, caused by migration of the cells, counteracts sedimentation. In order to obtain the necessary degree of separation there is thus required a long centrifuging time, which, in turn, again increases the morphological alteration of the cells.

There is attained a proper separation of the particles from the liquid and there is extensively avoided the remixing effect if the centrifuge tubes, during standstill of the rotor, reposition themselves into such a rest position under the influence of the force of gravity that their lengthwise axes are essentially vertically oriented, and further, if the centrifuge tubes and their holders, during the centrifuging action, pivot-out until reaching a stop or impact member, under the combined effect of the force of gravity and the centrifugal force, so that the lengthwise axes of the centrifuge tubes assume a predetermined inclined position. During run-up and run-down of the rotor the lengthwise axes of the centrifuge tubes, corresponding to the momentarily prevailing centrifugal force, continuously shift from the vertical or inclined position into the inclined or vertical position, as the case may be. Thus, during centrifuging the sediment is collected at the region of the floor or base of each tube. Morever, the path through which the particles must move until rouleaux formation is not as long as in the case of centrifuging with almost horizontal disposition of the lengthwise axes of the centrifuge tubes. During run-down of the rotor the separation surface between the sediment and the liquid, which is vertical during centrifuging and thus inclined with respect to the lengthwise axis of the centrifuge tubes, slowly and continuously shifts into the horizontal position which at the same time is located perpendicular to the lengthwise axis of each centrifuge tube. The remixing effect is extensively avoided by virtue of this slow and continuous positional change of the centrifuge tubes, and this is even more so by virtue of the fact that the centrifugal force, after the point in time where the holders no longer contact the stops, always acts in the direction of the lengthwise axes of the centrifuge tubes. Upon stoppage of the rotor the centrifuge tubes are oriented so that each lengthwise axis is vertically dispositioned. There are thus combined the advantages of the individually known centrifuge methods, without having to take into account their drawbacks. The end result of such is that, on the one hand, there is obtained a shorter centrifuging time, and thus, a lesser morphological change of the particles (if such for instance are erythrocytes), and, on the other hand, there is realized an optimum suppression of the remixing between the sediment and the remaining liquid.

It is however necessary to be able to adjust the inclined position of the centrifuge tubes between almost 0° and 90° in order to optimumly accommodate the momentary requirements of the samples to be centrifuged (in accordance with the blood dilution, the tube diameter and so forth). From U.S. Pat. Nos. 2,739,759, 3,722,789 and 3,951,334 there have become known to the art centrifuges wherein there are adjustably arranged at the rotor screws serving as stops for limiting the outward pivoting or rocking of the centrifuge tubes and their holders. These known stops must be however individually adjusted, so that it is difficult to avoid different settings of the stops and the corresponding imbalance at the rotor. Also, such type stops can tend to alter their setting during centrifuging, and finally, it is cumbersome to change the setting of the stops for accommodating different requirements and to again properly reset the stops to a previous setting after a change has been made. Furthermore, from the aforementioned U.S. Pat. No. 2,739,759 it is known to construct the stops in each case as contact locations of a disk-shaped body equipped with slots and the pivoted-out centrifuge tubes. During the pivoting-out movement each respective centrifuge tube is radially guided in one of the slots. With this design the stops or impact members however are not adjustable.

SUMMARY OF THE INVENTION

Therefore, with the foregoing in mind it is a primary object of the present invention to provide a new and improved construction of a centrifuge of the previously mentioned type wherein the aforementioned drawbacks and limitations of the prior art proposals are extensively overcome.

Another and more specific object of the present invention is to construct a centrifuge of the previously mentioned type wherein there are practically eliminated different settings of the individual stops or impact members and there can easily again be reestablished predetermined stop settings.

Now in order to implement these and still further objects of the invention, which will become more readily apparent as the description proceeds, the centrifuge of the present development for separating particles suspended in a liquid, especially although not exclusively for use in the separation of erythrocytes in a blood sample, comprises a rotor which is rotatable about a substantially vertical axis. At the rotor there are arranged a number of holders for related centrifuge tubes each containing the liquid. The holders are pivotably mounted about a respective substantially horizontal axis. During standstill of the rotor the holders are located in a rest position and upon rotation of the rotor the holders rock-out of this rest position under the action of the centrifugal force. Arranged at the rotor are stops or impact members for limiting the pivoting-out of the holders. Each stop is structured as a contact location between a pivoted-out holder and a body arranged at and surrounding the rotor. This body is arranged at the rotor so as to be displaceable and fixable in position.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 5 is a side view of a holder for a centrifuge tube or the like.

DETAILED DESCRIPTION OF THE PREFERRED EMBODIMENTS

Figure 1:
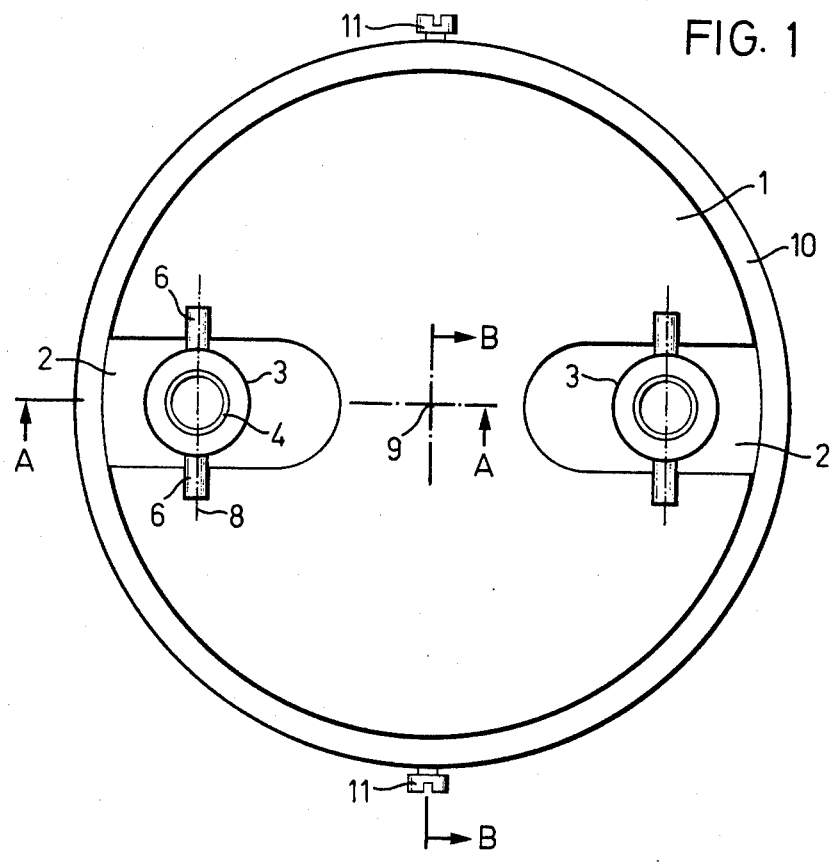
FIG. 1 is a top plan view of a rotor of a centrifuge according to the invention and having two respective mounted holders and centrifuge tubes, the centrifuge being shown in its standstill position.

Describing now the drawings, it is firstly here mentioned that to simplify the illustration there have only been shown the parts of the centrifuge which are necessary for explaining the function and underlying principles of the invention. Other parts, such as the bearings, drive and the like, which may be conventional and not directly concerned with the principles of the invention, have been conveniently omitted. Throughout the various Figures the same elements have been generally designated by the same reference characters.

Turning attention now to FIG. 1 in particular, a rotor of the centrifuge has been generally designated by reference character 1. The rotor 1 is provided with two recesses or pockets 2 each capable of receiving therein a holder 3 for a related centrifuge tube 4 or equivalent structure. The lengthwise axis of each centrifuge tube 4 has been designated by reference character 5. Each holder or support 3 is equipped with two axle journals or pivot shafts 6, by means of which each such holder 3 can be mounted in appropriate, upwardly open recesses 7 of the rotor 1 so as to be pivotably supported for movement about a horizontal pivot axis 8. The vertical axis of rotation of the rotor 1 has been designated by reference character 9.

Figure 2:
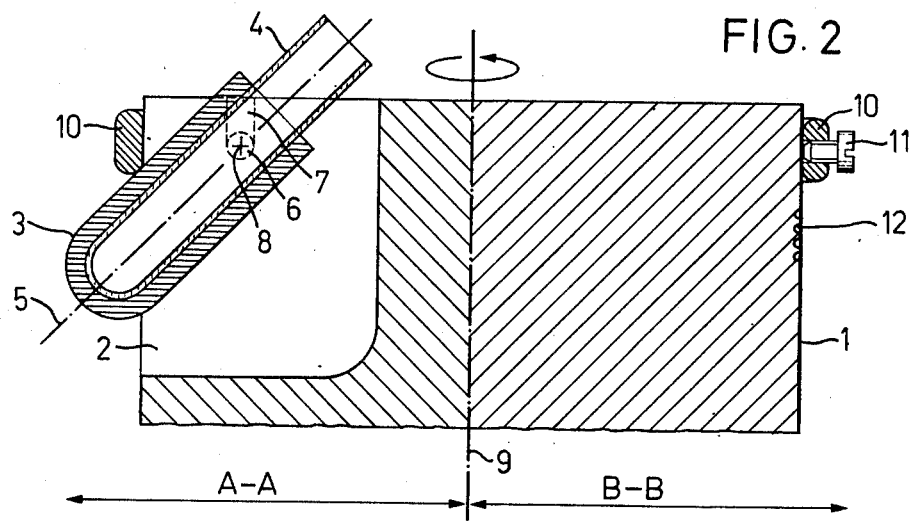
FIG. 2 respectively show sectional views of a part of the rotor, a holder and a centrifuge tube taken along the lines A—A and B—B of FIG. 1, during the maximum rotational speed of the rotor.
Figures 3A, 3B:
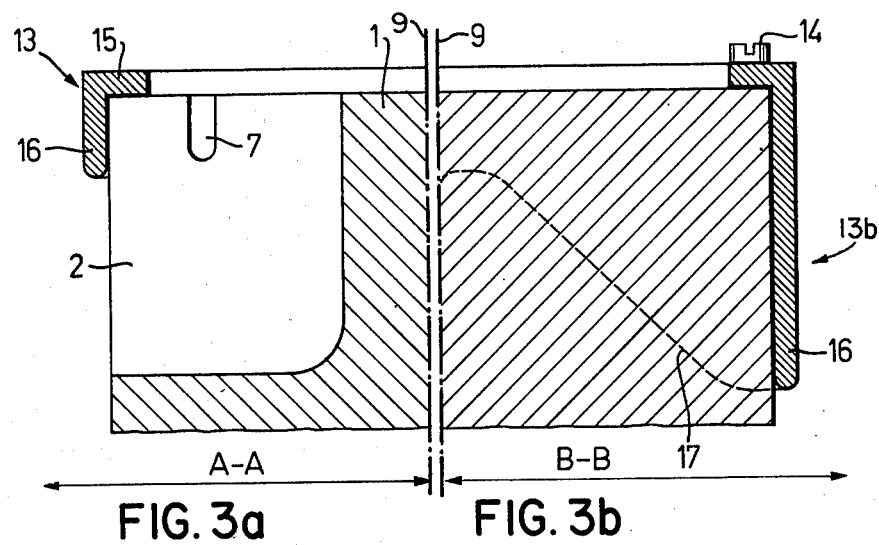
FIGS. 3a and 3b are respective sectional views of a part of the rotor, again taken along the lines A—A and B—B of FIG. 1, showing two modified constructions of the stops or impact members which have been grouped together into a ring-shaped body.

FIGS. 1 and 2 illustrate a ring or ring member 10 which is displaceably arranged at the rotor 1 in a direction essentially parallel to the rotational axis 9 and can be arrested at any desired height along the rotor 1 by means of the fixing screws 11 or equivalent structure. Details of the arresting mechanism are not necessary or important to the invention, since it will be readily evident that any suitable arresting or fixing means can be used. Furthermore, it is to be understood that conventional techniques can be resorted to in order to avoid imbalance, paarticularly through the loss of the screws or the like during centrifuging. The ring member 10 serves as a stop or impact member for each holder 3 during the action of a pronounced centrifugal force by virtue of the high rotational speed of the rotor 1. This has been shown at the left-hand side of FIG. 2 in particular. The stop is formed by the contact location between the holder 3 and the ring 10. In the showing of FIG. 1 the ring or ring member 10 has approximately the shape of a band, but it also can have a circular or round cross-sectional configuration or form another body of revolution. At the outer surface of the rotor 1, for instance at the location generally designated by reference character 12, there is applied or engraved or otherwise provided a suitable scale serving to indicate the position of the ring member 10, so that such can be recorded and again set at any desired position. Instead of using the ring 10 there also can be provided individual stops for each holder, these stops being variable in their position. Yet, the illustrated construction employing a ring member or ring 10 preferred.

Figures 4A, 4B:
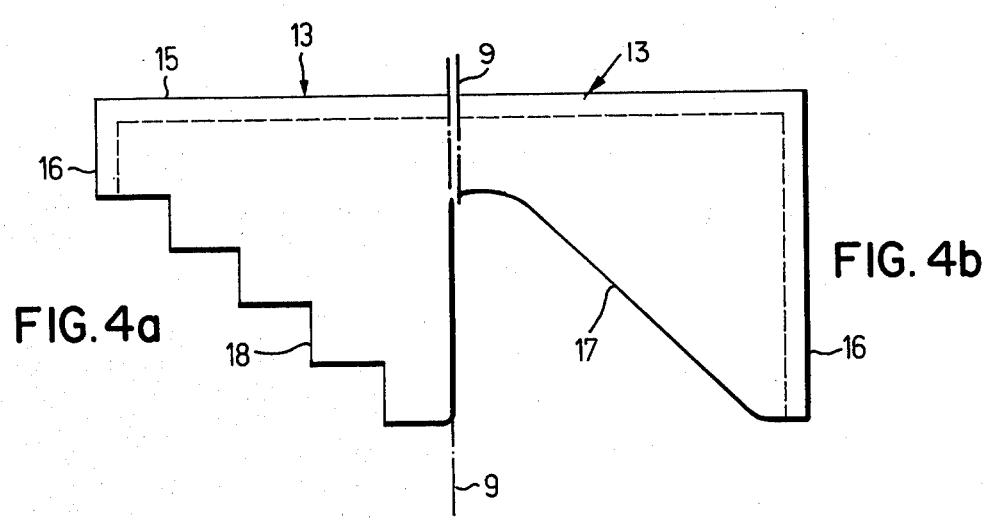
FIGS. 4a and 4b are respective side views of the ring-shaped bodies shown in FIGS. 3a and 3b.
Figure 5:
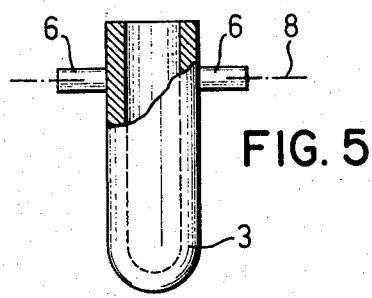

Further particular embodiments of the inventive centrifuge have been shown in FIGS. 3a, 4a and 3b, 4b wherein a sleeve 13 is arranged at the rotor 1. This sleeve or sleeve member 13 can be secured at the rotor 1 by means of fixing or setting screws 14 or equivalent structure in such a manner that the sleeve 13 snugly bears by means of its upper portion 15 and its lateral portion 16 at the rotor 1. As best seen by referring to the embodiment of FIGS. 3b, 4b, the lower portion or part 17 of the sleeve 13 has a sawtooth-shaped configuration, and the periodicity of the sawtooth shape over the circumference of the sleeve 13 and the rotor 1 corresponds to the distribution of the holders or supports 3 at the rotor 1. The not particularly referenced boundary surface of the sleeve 13 at the lower part 17 serves as an adjustable stop or impact means for each holder 3. For this purpose the sleeve 13 is rotated in relation to the rotor 1 such contact between the sleeve 13 and the holder 3 which is to be rocked out occurs at the desired height, whereafter the sleeve 13 is arrested at the desired position by the fixing screws 14. Also with this construction there is mounted or engraved or otherwise applied a scale, like in FIG. 2, at the rotor 1, for instance approximately at the position designated by reference character 12 and schematically indicating such scale. This scale 12 either can indicate in vertical direction the height of the boundary surface of the lower portion or part 17 of the sleeve 13 or in horizontal direction the angular position of the sleeve 13 in relation to the rotor 1, so that there can be recorded and again set the position of the sleeve 13. According to a modification, the lower part of the sleeve 13, while retaining the general sawtooth-shape, can be provided with steps or stepped portions, as illustrated in FIG. 4a by the stepped lower part 18 of the sleeve 13. This construction facilitates the precise adjustment of the stops.

The mode of operation of the inventive centrifuge can be explained as follows in conjunction with an example relating to the centrifuging of a blood sample. With increasing rotational speed of the rotor 1 the holders or supports 3 for the centrifuge tubes 4 pivot under the action of the centrifugal force to an ever increasing extent towards the outside, until they contact the ring 10 or the sleeve 13 functioning as stop means, and thus, are fixed in a predetermined position. The separated erythrocytes collect at the neighborhood of the floor or base of each centrifuge tube 4. After completion of the centrifuging time needed for the separation the rotational speed again decreases and the centrifugal force becomes correspondingly smaller. This in turn causes the initially almost vertically dispositioned separation surface between the sediment and the remaining liquid to become increasingly more inclined. Once the rotational speed has dropped to such an extent that the holders 3 no longer contact the stop means, then the separation surface is inclined to such an extent that it is disposed almost perpendicular to the lengthwise axis 5 of the related centrifuge tube 4, and it remains in this position regardless of the direction at which the holder adjusts itself under the combined effect of the force of gravity and the centrifugal force. During the run-down of the rotor the sample always is under the influence of a force which is effective in the direction of the lengthwise axis 5 of the related centrifuge tube 4 and the tube base, which, in turn, prevents the occurrence of the remixing effect. With further decreasing rotational speed and corresponding decrease of the centrifugal force the holders 3 always rock more and more back into their vertical rest position. The sediment has adequate time to slowly shift into a position having an essentially horizontal separation surface, and has reached this position when the rotor 1 comes to standstill. The sediment and/or the liquid then can be immediately further used or processed.

While there are shown and described present preferred embodiments of the invention, it is to be distinctly understood that the invention is not limited thereto, but may be otherwise variously embodied and practiced within the scope of the following claims. Accordingly

What we claim is:

1. A centrifuge for separating particles suspended in a liguid, especially for the separation of erythrocytes contained in a blood sample, comprising:

a rotor rotatable about a substantially verticle axis of rotation;

a number of holders each capable of supporting a centrifuge tube containing a liquid;

means mounting each of said holders at the rotor to be pivotable about a substantially horizontal axis;

said holders being located in a rest position when the rotor is stationary and upon rotation of the rotor pivoting out of this rest position under the action of the centrifugal force resulting from rotation of the rotor;

stop means for selectively limiting the pivoting-out movement of the holders;

said stop means comprising one single body member arranged at and surrounding said rotor and coming into contact with each pivoted-out holder at a respective contact location at the related pivoted-out holder;

said single body member being displaceably arranged at said rotor; and means for positionally fixing said single body member at the rotor.

2. The centrifuge as defined in claim 1, wherein:

said single body member includes a lower portion having sawtooth-shaped boundary means.

3. The centrifuge as defined in claim 1, wherein:

said single body member includes a lower portion having sawtooth-shaped boundary means provided with stepped portions.

4. The centrifuge as defined in claim 1, further including:

scale means for indicating the position of the single body member at the rotor.

* * * * *

UNITED STATES PATENT AND TRADEMARK OFFICE
CERTIFICATE OF CORRECTION

PATENT NO. : 4,221,324
DATED : Sep. 9, 1980
INVENTOR(S) : ADRIAN LORENZ and RAYMOND FREY It is certified that error appears in the above–identified patent and that said Letters Patent are hereby corrected as shown below:

On the title page, [76] Inventor, change

"Inventor: Raymond Frey, Zürich, Switzerland" to read:

--Inventors: Adrian Lorenz and Raymond Frey, Zürich, Switzerland--

Signed and Sealed this

Third Day of February 1981

[SEAL]

*Attest:*

*Attesting Officer*

RENE D. TEGTMEYER

*Acting Commissioner of Patents and Trademarks*